United States Patent [19]

Tanaka et al.

[11] Patent Number: 4,778,514

[45] Date of Patent: Oct. 18, 1988

[54] N-ACYL AMINO ACID DERIVATIVE AND PROCESS FOR PRODUCTION AND USE THEREOF

[75] Inventors: Takaharu Tanaka, Osaka; Naoki Higuchi, Ikeda; Masayuki Saito; Masaki Hashimoto, both of Ibaraki, all of Japan

[73] Assignee: Suntory Limited, Osaka, Japan

[21] Appl. No.: 871,556

[22] Filed: Jun. 6, 1986

[30] Foreign Application Priority Data

Jun. 8, 1986 [JP] Japan .................................. 60-123494

[51] Int. Cl.[4] .................... A01N 37/36; C07C 101/30
[52] U.S. Cl. .......................................... 71/108; 71/115; 71/116; 560/39; 562/444
[58] Field of Search ..................... 560/39, 45; 71/108, 71/115, 116; 562/444

[56] References Cited

U.S. PATENT DOCUMENTS 3,364,249 1/1968 Bolhofer ............................... 560/39
4,382,954 5/1983 Chan ....................................... 560/9

FOREIGN PATENT DOCUMENTS 1544786 11/1968 France .

OTHER PUBLICATIONS

Journal of the Chemical Society, Perkin Transactions 1, Organic and Bio-Organic Chemistry, No. 11, 1973, pp. 1134–1136; C. Gallina et al.; "Synthesis of 2-alkoxy-2-acylaminopropionic acids by alkoxymercuration-demercuration of 2-acylaminoacrylic acids" (p. 1134).

Primary Examiner—Donald B. Moyer
Assistant Examiner—Bruce D. Gray
Attorney, Agent, or Firm—Burns, Doane, Swecker & Mathis

[57] ABSTRACT

N-halogenophenoxyacetyl amino acid or ester thereof and salt thereof, a process for production thereof comprising acylation of amino acid or derivative thereof, a herbicidal composition comprising the compound, and a method for killing or controlling plants using the compound. The compounds have a selective herbicidal effect.

7 Claims, No Drawings

N-ACYL AMINO ACID DERIVATIVE AND PROCESS FOR PRODUCTION AND USE THEREOF

BACKGROUND OF THE INVENTION

1. Field of the Invention

The present invention relates to a novel N-acyl amino acid derivative, and a process for the production and use thereof. The derivative exhibits a strong herbicidal activity, and is useful as an active ingredient for various kinds of agricultural chemicals.

2. Description of the Related Art

A series of phenoxy compounds including 2,4-dichlorophenoxyacetic acid, 2-methyl-4-chlorophenoxyacetic acid, and the like have been used as herbicides important for agriculture and gardening. Novel, L., French Pat. No. 1,544,786, discloses p-halogenophenoxyacetic acid compounds. The biological actions of these phenoxy herbicides mainly rely on the destruction in vivo of the auxin balance, which provides a disturbance of the fundamental physiological actions in a plant, including abnormal cell division, abnormal morphology, inhibition of chlorophyll formation, and abnormal cell walls, resulting in a rise of the osmotic pressure. Since the auxin hormone type herbicides can be applied to soil as well as the stem and leaves of a plant, and transported within a plant, such herbicides exhibit a herbicidal action on perennial weeds in, for example, a rice field, on which other types of herbicides have no herbicidal action. Moreover, the auxin hormone type herbicides strongly inhibit regeneration of the treated weeds.

Such phenoxy type herbicides, however, can provide undesirable side effects on important crops such as rice, wheat, barley, and the like, and are not effective on some perennial weeds, and therefore, are used only for limited applications and by limited methods.

SUMMARY OF THE INVENTION

Therefore, the present invention is directed to a novel phenoxy type herbicide which provides no or very little undesirable side effects on important crops including rice, wheat, barley and the like, exhibits a selective herbicidal effect on monocotyledons and broad-leaved plants and is stable when applied, maintaining the above-mentioned advantages of the phenoxy type herbicides, which herbicide is a condensation product of phenoxyacetic acid and an amine or amino acid.

More particularly, the present invention provides a compound having the formula (I), which compound exhibits a herbicidal effect.

The present invention also provides a process for the production of the compound having the formula (I).

The present invention also provides a herbicidal composition containing said compound as an active ingredient.

The present invention also provides a method for killing or controlling weeds.

DESCRIPTION OF THE PREFERRED EMBODIMENT

The present N-acyl amino acid derivative has the following general formula (I):

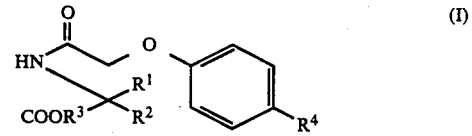

wherein $R^1$ represents an alkyl group having 1 to 4 carbon atoms, and $R^2$ represents a straight-chain or branched chain alkyl group having 1 to 10 carbon atoms, or a straight-chain or branched chain alkyl group having 1 to 5 carbon atoms substituted by a carboxyl group; or $R^1$ and $R^2$, together with the carbon atom to which they bond, form a 3 to 10 membered ring structure optionally substituted by an alkyl group having 1 to 4 carbon atoms; or $R^1$ and $R^2$, together with the carbon atom to which they bond, form a vinylidene group optionally substituted by one or two straight-chain or branched chain alkyl groups having 1 to 6 carbon atoms; $R^3$ represents a hydrogen atom or an alkyl group having 1 to 4 carbon atoms; and $R^4$ represents a halogen atom, and salts thereof.

The alkyl group as represented by $R^1$ and $R^3$ includes methyl, ethyl, propyl, and butyl groups.

The alkyl group as represented by $R^2$ includes, in addition to the alkyl groups as defined for $R^1$, pentyl, hexyl, octyl, nonyl and decyl groups, and the branched isomers thereof, such as isopropyl, isobutyl, tert-butyl, isopentyl, and the like.

The carboxy-substituted alkyl group as represented by $R^2$ includes carboxymethyl, 1-carboxyethyl, 2-carboxyethyl, 1-carboxypropyl, 2-carboxypropyl, 4-carboxybutyl, 5-carboxypentyl, and the like.

The ring structure formed by $R^1$ and $R^2$ together with the carbon atom to which $R^1$ and $R^2$ bond includes cyclopropylidene, cyclobutylidene, cyclopentylidene, cyclohexylidene, cycloheptylidene, cyclooctylidene, cyclononylidene, and cyclodecylidene.

The vinylidene group formed by $R^1$ and $R^2$ together with the carbon atom to which $R^1$ and $R^2$ bond includes vinylidene, methylvinylidene, dimethylvinylidene, ethylvinylidene, diethylvinylidene, isopropylvinylidene, di-isopropylvinylidene, and methylisopropylvinylidene groups, and the like.

The halogen as represented by $R^4$ includes fluorine, chlorine, bromine, and iodine.

The above-mentioned N-acyl amino acid derivative is produced, for example, by:

(1) reacting an amino acid derivative represented by the following general formula (II):

wherein $R^1$, $R^2$, and $R^3$ have the same meanings as defined for the formula (I), with a carboxylic acid or a derivative thereof represented by the following formula (III):

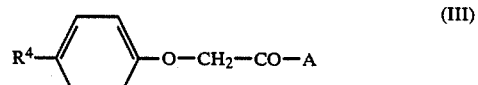

wherein R[4] has the same meaning as defined for the formula (I); and A represents a hydroxyl group, a halogen atom or an active ester group; in the presence or absence of a base in water or an organic solvent; or (2) reacting the amino acid derivative (II) described above with a carboxylic anhydride represented by the following formula (IIIa):

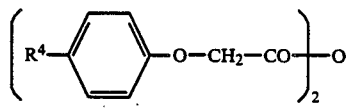

wherein R[4] has the same meaning as defined for the formula (I), in the presence or absence of a base in water or an organic solvent.

The base used for the above-mentioned reaction is preferably an alkaline metal hydroxide such as sodium hydroxide, potassium hydroxide or lithium hydroxide, or a trialkylamine such as trimethylamine, triethylamine, dimethylethylamine, methyldiethylamine or the like.

The reactions are preferably carried out at a temperature lower than room temperature for 1 to 12 hours with stirring.

In another embodiment, the N-acyl amino acid derivative of the present invention may be produced by condensing an amino acid ester of the following formula (IIa):

wherein R[1] and R[2] have the same meanings as defined for the formula (I), and R[5] represents an alkyl group having 1 to 4 carbon atoms, with a carboxylic acid of the following formula (III$_1$):

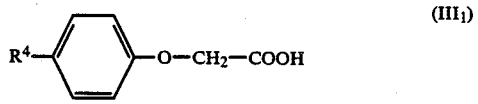

wherein R[4] has the same meaning as defined for the formula (I), by using a conventional condensation agent used for peptide synthesis, such as N-ethyl-N',N'-diaminopropylcarbodiimide, dicyclohexylcarbodiimide, or the like.

A typical embodiment for the production of the present compound comprises reacting an acid chloride which is already available or easily synthesized and has the following formula (III$_2$):

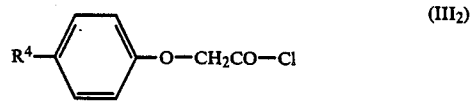

with the above-mentioned amino acid derivative of the formula (II) in an aqueous alkaline metal hydroxide solution.

The present compound thus synthesized is purified according to a conventional purification process, such as column chromatography, preparative thin-layer chromatography, and the like.

The present compound of the general formula (I) having a carboxyl group can be converted to corresponding salts thereof, such as sodium salt, potassium salt, lithium salt, and ammonium salt, by treating the compound (I) with sodium hydroxide, potassium hydroxide, lithium hydroxide, and aqueous ammonia respectively.

The compound of the present invention has weak toxicity of humans and domestic animals, and exhibits a highly specific and strong growth-inhibiting effect on monocotyledons or broad-leaved plants. Therefore, the present compound may be widely used as an agricultural chemical.

When the compound of the present invention is used as a herbicide, it may be used by mixing with a solid carrier such as clay or diatomaceous earth, or with a liquid carrier, such as water, or alcohols such as ethanol, propanol or butanol, aromatic hydrocarbons such as benzene, toluene or xylene, ethers such as dimethoxyethan or dioxane, ketons such methylethyl ketone, or esters such as ethyl acetate or butyl acetate. Alternatively, the present compound may be formulated into emulsions, suspensions, powders, wettable powders, granules, concentrated emulsions, and the like. The formulations are prepared according to a conventional procedure such as dissolving, mixing, milling, granulating, and the like, using the above-mentioned carrier, if necessary by adding an emulsifying agent, suspending agent, dispersing agent, stabilizing agent, spreader agent or the like. The herbicidal formulations can contain, in addition to the present compound, another kind of herbicide, insecticide, plant-growth regulator, or the like. Usually, such formulations contain 0.5 to 90% by weight of the present compound.

The amount of the present compound used as a herbicide varies depending upon the kinds of weeds to be killed, kind of crop to be protected, etc., and is usually 20 g to 500 g per 10 ares.

EXAMPLES

The present invention will now be further illustrated by, but is by no means limited to, the following examples.

EXAMPLE 1

N-(p-chlorophenoxy)acetyl-α,β-dehydrohomoalanine
(Compound SUAM 3500)

10 m moles of L-threonine was dissolved in 10 ml of 1N sodium hydroxide, and the solution was diluted to 20 ml with water. To the aqueous solution, 10 m moles of p-chlorophenoxyacetyl chloride dissolved in 10 ml of benzene was dropwise added with cooling and stirring. Immediately after, 10 ml of additional 1N sodium hydroxide aqueous solution was added. The reaction mixture was then allowed to warm to a room temperature, and was stirred for one day.

After the reaction was completed, the mixture was extracted twice with ethyl ether to eliminate unreacted p-chlorophenoxychloride, and the extracted aqueous phase was acidified with hydrochloric acid to precipitate a product which was then extracted three times with ethyl acetate. The extract was evaporated to dryness, and the residue was recrystallized from ethyl acetate/benzene/hexane to obtain a color-less crystal of N-(p-chlorophenoxy)acetyl-L-threonine. To a solution of 5 m moles of N-(p-chlorophenoxy)acetyl-L-threonine in ethyl ether, a solution of an excess amount of diazomethane in ethyl ether was added, and the mixture was allowed to stand for 30 minutes at a room temperature. The mixture was evaporated to dryness under a reduced pressure to obtain N-(p-chlorophenoxyacetyl)-L-threonine methyl ester. 3.4 m moles of N-(p-chlorophenoxyacetyl)-L-threonine methyl ester was dissolved in dried pyridine, and the resulting solution was added with 3.6 m moles of p-toluenesulfonyl chloride, stirred at 0° C. for two hours and at a room temperature for two hours. The reaction mixture was then partitioned between water and ethyl acetate, and organic phase was washed with 1N hydrochloric acid and water, and dried on anhydrous sodium sulfate. The solution was evaporated to dryness, and the resulting residue was purified by a middle pressure column chromatography with silica gel to obtain N-(p-chlorophenoxyacetyl)-O-(p-toluenesulfonyl)-L-threonine methyl ester. 0.5 m moles of N-(p-chlorophenoxyacetyl)-O-(p-toluenesulfonyl)-L-threonine methyl ester was then dissolved in 10 ml of methanol, the resulting solution was added with 1.5 ml of 1N sodium hydroxide and stirred for 20 minutes at a room temperature, and methanol was distilled off. The residue was acidified with 1N hydrochloric acid, and extracted with ethyl ether, and an organic phase was dried on anhydrous magnesium sulfate. Solvent was distilled off from the mixture to obtain a residue. The residue was then chromatographically purified to obtain the title compound N-(p-chlorophenoxyacetyl)-$\alpha,\beta$-dehydrohomoalanine.

Example 2

N-(p-chlorophenoxy)acetyl-$\alpha,\beta$-dehydrovaline methyl ester (Compound SUAM 3501)

10 m moles of L-valine was dissolved in 10 ml of 1N sodium hydroxide, and the resulting solution was diluted with water to 20 ml. To the aqueous solution, 10 m moles of p-chlorophenoxyacetyl chloride dissolved in 10 ml of benzene was slowly added dropwise, with cooling and stirring. Immediately after, 10 ml of additional sodium hydroxide aqueous solution was added. The reaction mixture was allowed to warm to a room temperature, and stirred at a room temperature for one day.

After the reaction was completed, the mixture was extracted twice with ethyl ether to eliminate the unreacted acid chloride, and the extracted aqueous phase was acidified with hydrochloric acid to precipitate a product, which was then extracted three times with ethyl acetate, the extract was evaporated to dryness, and the residue was recrystallized from ethyl acetate/benzene/hexane to obtain a color-less crystal of N-(p-chlorophenoxy)acetyl-L-valine. 10 m moles of the crystalline compound was then dissolved in ethyl ether, the resulting solution was added with a solution of an excess amount of diazomethane in ethyl ether, and solvent was distilled off to obtain N-(p-chlorophenoxy)acetyl-L-valine methyl ester. 6.7 m moles of the ester was dissolved in 10 ml of dried toluene, and the resulting solution was added dropwise with 6.7 m moles of tert.-butoxyhypochloride, and then added with potassium tert.-butoxide, and the mixture was stirred for 30 minutes at a room temperature. The reaction mixture was partitioned between chloroform and water, the organic phase was washed with water, and then dried on anhydrous sodium sulfate. The dried solution was evaporated to dryness under reduced pressure to obtain a residue which was purified by middle pressure chromatography with silica gel to obtain N-(p-chlorophenoxy)acetyl-N-chloro-L-valine methyl ester.

3.3 m moles of the N-(p-chlorophenoxy)acetyl-N-chloro-L-valine methyl ester was dissolved in 10 ml of dried benzene, and the resulting solution was added dropwise with 3.3 m moles of 1,8-diazabicyclo[5,4,0]-7-undecene, and stirred for 15 minutes at a room temperature. The reaction mixture was evaporated to dryness, and the resulting residue was dissolved in chloroform. The resulting solution was washed with diluted hydrochloric acid, saturated sodium chloride solution, saturated sodium bicarbonate solution, and again with a saturated sodium chloride solution, in this order, and dried on anhydrous sodium sulfate. The dried solution was evaporated under a reduced pressure, and the residue was purified by middle pressure chromatography with silica gel to obtain the title compound N-(p-chlorophenoxy)acetyl-$\alpha,\beta$-dehydrovaline methyl ester.

Example 3

N-(p-chlorophenoxy)acetyl-$\alpha$-dimethylglycine (Compound SUAM 3502)

10 m moles of $\alpha$-dimethylglycine was dissolved in 10 ml of 1N sodium hydroxide, and the resulting solution was diluted to 20 ml with water. To the solution, 10 m moles of p-chlorophenoxyacetyl chloride dissolved in 10 ml of benzene was slowly added dropwise with ice-cooling and stirring. Immediately after, 10 ml of additional 1N sodium hydroxide solution was added. The reaction mixture was allowed to warm to a room temperature, and stirred at a room temperature overnight.

After the reaction was completed, the mixture was extracted twice with ethyl ether to eliminate unreacted p-chlorophenoxyacetyl chloride, and the extracted aqueous phase was acidified with hydrochloric acid to precipitate a product, which was then extracted three times with ethyl acetate, the extract was evaporated, and the residue was recrystallized from ethyl acetate/benzene/hexane to obtain a color-less crystal of the title compound.

Example 4

N-(p-chlorophenoxy)acetyl-DL-$\alpha$-methylglutanic acid (Compound SUAM 3503)

10 m moles of DL-$\alpha$-methylglutanic acid was dissolved in 20 ml of 1N sodium hydroxide aqueous solution, and the resulting solution was diluted with water to 40 ml.

According to the same procedure as described in Example 3, the title compound was obtained as a color-less crystal.

Example 5

N-(p-chlorophenoxy)acetyl-$\alpha,\beta$-dehydroalanine methyl ester (Compound SUAM 3507)

Example 3 was repeated except that 10 m moles of L-serine was used in place of $\alpha$-dimethylglycine to obtain N-(p-chlorophenoxy)acetyl-L-serine as a color-less crystal.

10 m moles of the crystalline compound was dissolved in ethyl, and to the solution, a solution of an excess amount of diazomethane in ethyl ether was added. Solvent was distilled off to obtain N-(p-chlorophenoxy)acetyl-L-serine methyl ester.

10 m moles of this compound was dissolved in 30 ml of chloroform, and the resulting solution was added with 1.6 ml of dimethylformamide and 0.8 ml of thionyl chloride, and refluxed for one hour. After the reaction was completed, the reaction mixture was evaporated to eliminate the solvent, and added with 50 ml of petroleum ether to generate a precipitate. The mixture was filtered to collect the precipitate, which was then washed with petroleum ether, and dried to obtain N-(p-chlorophenoxy)acetyl-L-($\beta$-chloro)alanine methyl ester.

A suspension of 6.7 m moles of sodium methoxide in 30 ml of dried benzene was refluxed, and during the reflux, the suspension was added dropwise with a solution of 6.5 m moles of N-(p-chlorophenoxy)acetyl-L-($\beta$-chloro)alanine methyl ester dissolved in 5 ml of dried benzene. The reaction mixture was refluxed for 5 hours, washed with water, and dried with anhydrous magnesium sulfate. The dried solution was evaporated to eliminate solvent and to form a crystal. The crystal was then washed with carbon tetrachloride to obtain the title compound N-(p-chlorophenoxy)acetyl-$\alpha,\beta$-dehydroalanine methyl ester.

Example 6

N-(p-chlorophenoxy)acetyl-1-aminocyclopentane carboxylic acid (Compound SUAM 3504)

50 m moles of cyclopentanon was dissolved in about 200 ml of 50% aqueous ethanol, and to the resulting solution was added one equivalent amount of ammonium carbonate and one equivalent amount of sodium cyanide. The solution was heated for about two hours at 58° C.~60° C. in a reactor equipped with a condenser, and then cooled. After the solution was concentrated to about ⅔ of the original volume, white crystals appeared. The mixture was then cooled on ice-water for full crystallization. The crystal was then filtered off and dried to obtain cyclopentane-5'-spirohydantoin. 20 m moles of the hydantoin and two equivalent amounts of barium hydroxide were suspended in 200 ml of water, and the suspension was heated to reflux for 3 hours at about 160° C. using a condenser. The reaction mixture was allowed to cool, resulting in the formation of a precipitate of barium carbonate, and filtrated to eliminate the precipitate. The resulting aqueous filtrate was added with an excess amount of ammonium carbonate, and stirred for an hour to precipitate unreacted barium hydroxide. The mixture was again filtrated to eliminate the precipitate. The filtrate was concentrated to crystallize 1-aminocyclopentane carboxylic acid, and the crystal was filtered off and dried. 1-aminocyclopentane carboxylic acid thus obtained was used to obtain the title compound according to the same procedure as described in Example 3.

Example 7

According to the same procedure as described in Example 6, the following compounds were prepared.

N-(p-chlorophenoxy)acetyl-1-aminocyclobutane carboxylic acid (Compound SUAM 3505);

N-(p-chlorophenoxy)acetyl-1-aminocycloheptane carboxylic acid (Compound SUAM 3506);

N-(p-chlorophenoxy)acetyl-1-aminocyclohexane carboxylic acid (Compound SUAM 3508);

N-(p-chlorophenoxy)acetyl-1-amino-4-methylcyclohexane carboxylic acid (SUAM 3509);

N-(p-chlorophenoxy)acetyl-1-amino-cyclooctane carboxylic acid (SUAM 3510).

The physico-chemical properties of the compounds prepared by Examples 1 to 7 are set forth in Table 1.

TABLE 1

(structure: 4-chlorophenyl-O-CH2-C(=O)-NH-C(R1)(R2)-COOR3)

| (Exp. No.) SU.AM No. | | Substituent | Appearance | Melting point (°C.) | IR-Spectrum (KBr, cm⁻¹) | NMR-Spectrum (δ ppm, TMS) | Mass spectrum (m/z) | Elemental analysis |
|---|---|---|---|---|---|---|---|---|
| (1) 3500 | R¹ R² } R³ | =CH—CH₃  —H | Crystal | Decomposition | 3400, 1650, 1560, 1485, 1230, 825 | (CD₃OD), 1.67 (3H, d, J = 6.6 Hz), 4.61 (2H, s), 6.70 (1H, q, J = 6.6 Hz), 6.94 (2H, d, J = 9.6 Hz), 7.25 (2H, d, J = 9.6 Hz) | — | — |
| (2) 3501 | R¹ R² } R³ | =C(CH₃)(CH₃)  —H | Crystal | 116–116.5 | 1715, 1660, 1485, 1300, 1225, 830 | (CDCl₃), 1.84 (3H, s), 2.22 (3H, s), 4.57 (2H, s), 6.92 (2H, d, J = 9.1 Hz), | — | — |
| (3) 3502 | R¹ R² R³ | —CH₃ —CH₃ —H | Crystal | 206.5–207.5 | 3380, 1700, 1635, 1540, 1240, 1205, 820 | 7.34 (2H, d, J = 9.1 Hz), 7.62 (1H, s) (CD₃OD), 1.54 (6H, s), 4.46 (2H, s), 6.94 (2H, d, J = 9.1 Hz), 7.26 (2H, d, J = 9.1 Hz) | 271 (M⁺) | (C₁₄H₁₆NO₄Cl) Calc.  C 56.48  H 5.42  N 4.70 Found 56.67  5.25  4.92 |
| (4) 3503 | R¹ R² R³ | —(CH₂)₂—COOH —CH₃ —H | Crystal | 171.5–173 | 3360, 1715, 1635, 1490, 1240, 820 | (CD₃OD), 1.57 (3H, s), 2.24 (2H, m), 2.30 (2H, m), 4.48 (2H, dd, J = 15.0, 15.0 Hz), 6.98 (2H, d, J = 9.1 Hz), 7.27 (2H, d, J = 9.1 Hz) | — | (C₁₄H₁₆NO₄Cl) Calc.  C 53.05  H 5.19  N 5.16 Found 53.06  5.08  5.17 |
| (5) 3507 | R¹ R² } R³ | =CH₂  —CH₃ | Crystal | 86.5–87.5 | 1720, 1700, 1520, 1495, 1245, 830 | (CD₃OD), 3.83 (3H, s), 4.60 (2H, s), 5.90 (1H, s), 6.45 (1H, s), 6.98 (2H, d, J = 9.1 Hz), 7.30 (2H, d, J = 9.1 Hz) | — | — |
| (6) 3504 | R¹ R² } R³ | (cyclopentyl)  —H | Crystal | 148–152 | 3370, 1770, 1730, 1700, 1240, 820 | (CD₃OD), 1.8–1.1 (8H, m), 4.48, 4.62 (each s, 1H), 6.68, 6.92 (each 1H, d, J = 9.1 Hz), 7.23, 7.24 | 297 (M⁺) | C 51.00  H 4.89  N 4.25 Calc. Found 50.88  4.81  4.30 |
| (7) 3505 | R¹ R² } R³ | (cyclobutyl)  —H | Crystal | 168–173 (Decomposition) | 3390, 1720, 1695, 1620, 1240, 820 | (CD₃OD), 1.8–2.8 (6H, m), 4.48, 4.64 (each 1H, s), 6.94 (2H, d, J = 9.1 Hz), 7.25, 7.27 (each 1H, d, J = 9.1 Hz) | 283 (M⁺) | (C₁₄H₁₆NO₆Cl) — |

TABLE 1-continued

![structure: HN-C(=O)-CH with R1, R2, COOR3 and O-C6H4-Cl group]

| (Exp. No.) SUAM No. | Substituent R1, R2, R3 | Appearance | Melting point (°C.) | IR-Spectrum (KBr, cm$^{-1}$) | NMR-Spectrum (δ ppm, TMS) | Mass spectrum (m/z) | Elemental analysis |
|---|---|---|---|---|---|---|---|
| (7) 3506 | 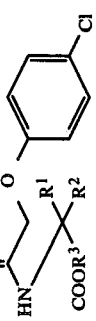 cyclohexyl, —H | Crystal | 132–134 | 3490, 3360, 2930, 1720, 1490, 1260, 1240, 820 | (CD$_3$OD), 1.56 (8H, m), 2.08 (4H, m), 4.50 (2H, s), 6.93 (2H, d, J = 9.1 Hz), 7.25 (2H, d, J = 9.1 Hz) | 325 (M$^+$) | — |
| (7) 3508 | cyclohexyl, —H | Crystal | 158–160 | 3265, 1710, 1660, 1220, 830 | (CD$_3$OD), 1.20–2.20 (10H, m), 4.54 (2H, s), 6.95 (2H, d, J = 9.1 Hz), 7.27 (2H, d, J = 9.1 Hz) | 331 (M$^+$) | — |
| (7) 3509 | 4-methylcyclohexyl, —H | Crystal | 223–224.5 (Decomposition) | 3430, 1720, 1645, 1245, 1210, 820 | (CD$_3$OD), 0.78 (3H, d, J 8.8 Hz), 0.9–2.3 (9H, m), 4.54 (2H, s), 6.97 (2H, d, J = 9.1 Hz), 7.28 (2H, d, J = 9.1 Hz) | 325 (M$^+$) | Calc.  C (%) 58.99  H (%) 6.19  N (%) 4.30<br>Found 58.96  6.17  4.34 |
| (7) 3510 | cycloheptyl | Crystal | 156–157 | 3275, 1700, 1655, 1225, 825 | (CD$_3$OD), 1.53 (10H, m), 2.08 (4H, m), 4.46 (2H, s), 6.95 (2H, d, J = 9.1 Hz), 7.36 (2H, d, J = 9.1 Hz) | 339 (M$^+$) | (C$_{16}$H$_{20}$NO$_4$Cl)<br>Calc. C (%) 60.09  H (%) 6.53  N (%) 4.12<br>Found 60.10  6.43  4.22 |

Example 8

The compounds of the present invention were evaluated for their selective herbicidal activity on broad-leaved plants, i.e., cucumber and radish, and monocatylenodons, i.e., rice, wheat, and barnyard grass.

The test was carried out as a before-germination test and an after-germination test.

For the before-germination test for cucumber and radish, five each of seeds of these plants were seeded in soil contained in a pot 6×15×15 cm in size. Immediately after the seeding, 60 ml per pot of aqueous acetone solution containing a predetermined amount of test compound was applied to the pot. The aqueous solution of the test compound was prepared so that the above-mentioned application provides 200 g or 50 g of the test compound per 10 ares. For the after-germination test, for cucumber and radish, the seeds thereof were germinated and grown in a greenhouse until each plant had two to three leaves, and the two lots of seedlings were transplanted to a pot as described for the before-germination test, and immediately after the transplanting, the test compound was applied as described above.

For the before-germination test for rice, barley and barnyard grass, ten each of seeds of these plant were seeded at a depth of 1 to 2 cm in soil from a rice field contained in a pot 20×10×6 cm in size, submerged to a depth of about 3 cm, and 60 ml of an aqueous solution of test compound was incorporated in the water in the pot. The aqueous solution was prepared so that the above-mentioned application provides 200 g or 50 g of the test compound per 10 ares. For the after-germination test for rice, barley and barnyard grass, the seeds thereof were germinated and grown in a greenhouse until each plant had 2 to 3 leaves, and the two lots of seedlings were transplanted to a pot as described for the before-germination test, and immediately after the transplanting, the test compound was applied as described above.

After the application of the test compounds, the growth of the plants was observed, and the herbicidal effect evaluated by scores of 5 (complete killing) to 0 (not effective). The results are set forth in Table 2.

As seen from Table 2, the compounds of the present invention exhibit a notable herbicidal effect.

In particular, the compound SUAM 3500 prepared according to Example 1 exhibits a selective herbicidal effect on monocotylenodons, and compounds SUAM 3501 to 3509 prepared according to Examples 2 to 7 exhibit a selective herbicidal effect on broad-leaved plants.

Example 9

Typical herbicidal compositions of the present invention were prepared as follows.

| Granule | |
|---|---|
| Ingredient | Amount (part by weight) |
| The present compound | 5.5 |
| Benitoite | 54.5 |
| Talc | 40.0 |

The above-mentioned ingredients were mixed homogeneously and milled. The mixture was added with a small amount of water and mixed to form a paste. The paste was then granulated and dried.

| Emulsion | |
|---|---|
| Ingredient | Amount (part by weight) |
| The present compound | 20 |
| Tween-80 | 5 |
| Span-80 | 5 |
| Solvent naphtha | 70 |

The above-mentioned ingredients were mixed to form an emulsion.

| Wettable powder | |
|---|---|
| Ingredient | Amount (part by weight) |
| The present compound | 50 |
| Diatomaceous earth | 30 |
| Clay | 10 |
| Sodium raulyl sulfate | 10 |

TABLE 2

| Test compound (Exp. No.) SUAM No. | Amount of application (g/10 ares) | Before-germination test | | | | | After-germination test | | | | |
|---|---|---|---|---|---|---|---|---|---|---|---|
| | | Broad-leaved plant | | Monocotylenodons | | | Broad-leaved plant | | Monocotylenodons | | |
| | | Cucumber | Radish | Rice | Wheat | Barnyard grass | Cucumber | Radish | Rice | Wheat | Barnyard grass |
| (1) 3500 | 200 50 | 5 4 | 5 5 | 5 4 | 4 2 | 4 3 | 2 0 | 3 0 | 5 4 | 4 3 | 5 4 |
| (2) 3501 | 200 50 | 5 5 | 5 5 | 3 2 | 5 3 | 5 4 | — | — | — | — | — |
| (3) 3502 | 200 50 | 5 5 | 5 4 | 3 2 | 3 2 | 4 2 | 5 5 | 5 5 | 3 0 | 2 0 | 3 0 |
| (4) 3503 | 200 50 | 5 3 | 5 3 | 0 0 | 0 0 | 0 0 | — | — | — | — | — |
| (5) 3507 | 200 50 | 5 5 | 5 5 | 3 0 | 3 0 | 4 2 | — | — | — | — | — |
| (6) 3504 | 200 50 | 5 5 | 5 4 | 4 4 | 5 3 | 5 4 | 5 4 | 5 3 | 4 2 | 3 0 | 4 2 |
| (7) 3505 | 200 50 | 5 4 | 5 4 | 4 1 | 4 0 | 5 2 | — | — | — | — | — |
| (7) 3506 | 200 50 | 5 5 | 5 4 | 0 0 | 3 0 | 4 2 | — | — | — | — | — |
| (7) 3508 | 200 50 | 5 5 | 4 4 | 5 2 | 4 2 | 4 2 | 5 5 | 5 4 | 2 0 | 0 0 | 2 0 |
| (7) 3509 | 200 50 | 5 3 | 4 2 | 2 0 | 0 0 | 2 2 | — | — | — | — | — |
| (7) 3510 | 200 50 | 4 2 | 4 2 | 0 0 | 0 0 | 0 0 | — | — | — | — | — |

The above-mentioned ingredients were mixed homogeneously.

We claim:

1. A N-acyl amino acid derivative having the following formula (I):

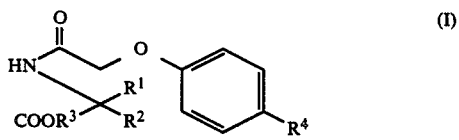

wherein $R^1$ and $R^2$, together with the carbon atom to which they bond, form a ring structure selected from the group consisting of cyclopropylidene, cyclobutylidene, cyclopentylidene, cyclohexylidene, cycloheptylidene, cyclooctylidene, cyclononylidene and cyclodecylidene groups; or $R^1$ and $R^2$, together with the carbon atom to which they bond, form a vinylidene group selected from the group consisting of vinylidene, methylvinylidene, dimethylvinylidene, ethylvinylidene, diethylvinylidene, isopropylvinylidene, di-isopropylvinylidene, and methyl-isopropylvinylidene groups; $R^3$ represents a hydrogen atom or an alkyl group having 1 to 4 carbon atoms; and $R^4$ represents a halogen atom, and salts thereof.

2. A N-acyl amino acid derivative according to claim 1 wherein $R^4$ selected from the group consisting of chlorine atom and bromine atom.

3. A N-acyl amino acid derivative according to claim 1 wherein the derivative is a salt selected from the group consisting of sodium salt, potassium salt, lithium salt, and ammonium salt.

4. A method for killing or controlling plants comprising applying an effective amount of an N-acyl amino acid derivative of the formula:

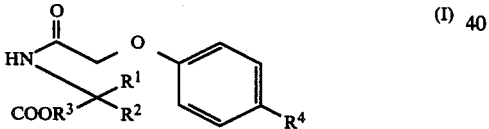

wherein $R^1$ represents an alkyl group having 1 to 4 carbon atoms, and $R^2$ represents a straight-chain or branched chain alkyl group having 1 to 10 carbon atoms, or a straight-chain or branched chain alkyl group having 1 to 5 carbon atoms substituted by a carboxyl group; or $R^1$ and $R^2$, together with the carbon atom to which they bond, form a 3 to 10 membered ring structure optionally substituted by an alkyl group having 1 to 4 carbon atoms, or $R^1$ and $R^2$, together with the carbon atom to which they bond, form a vinylidene group optionally substituted by one or two straight-chain or branched chain alkyl groups having 1 to 6 carbon atoms; $R^3$ represents a hydrogen atom or an alkyl group having 1 to 4 carbon atoms; and $R^4$ represents a halogen atom, to a medium in which plants to be killed or controlled would grow, or directly to plants to be killed or controlled.

5. A method according to claim 4 wherein the effective amount is 20 to 500 g per ares.

6. A method for killing or controlling plants comprising applying an effective amount of a herbicidal composition comprising (A) an effective amount of an N-acyl amino acid derivative having the formula (I):

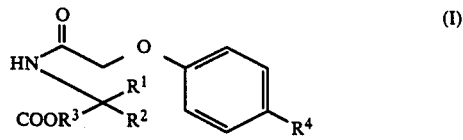

wherein $R^1$ represents an alkyl group having 1 to 4 carbon atoms, and $R^2$ represents a straight-chain or branched chain alkyl group having 1 to 10 carbon atoms, or a straight-chain or branched chain alkyl group having 1 to 5 carbon atoms substituted by a carboxyl group; or $R^1$ and $R^2$, together with the carbon atom to which they bond, form a 3 to 10 membered ring structure optionally substituted by an alkyl group having 1 to 4 carbon atoms; or $R^1$ and $R^2$, together with the carbon atom to which they bond, form a vinylidene group optionally substituted by one or two straight-chain or branched chain alkyl groups having 1 to 6 carbon atoms; $R^3$ represents a hydrogen atom or an alkyl group having 1 to 4 carbon atoms; and $R^4$ represents a halogen atom, and salts thereof and (B) a conventional carrier for herbicide.

7. A method according to claim 6 wherein the effective amount is 20 to 500 g per ares.

* * * * *